United States Patent [19]

McAuley

[11] Patent Number: 4,677,851

[45] Date of Patent: Jul. 7, 1987

[54] METHOD AND APPARATUS FOR MONITORING THE DENSITY OF A LIQUID

[76] Inventor: James A. McAuley, 8111 LBJ Freeway 190 1055, Dallas, Tex. 75251

[21] Appl. No.: 827,511

[22] Filed: Feb. 10, 1986

[51] Int. Cl.⁴ ............................................. G01N 9/04
[52] U.S. Cl. ...................................... 73/434; 177/208
[58] Field of Search ....................... 73/434, 433, 153; 177/208, 254

[56] References Cited

U.S. PATENT DOCUMENTS

| | | | |
|---|---|---|---|
| 1,575,643 | 3/1926 | Salich | 73/434 |
| 2,284,060 | 5/1942 | Knauth | 73/434 |
| 2,598,827 | 6/1952 | Pettigrove | 73/434 |
| 3,039,310 | 6/1962 | Copland et al. | 73/434 |
| 3,812,723 | 5/1974 | Barron | 73/434 |
| 3,866,464 | 2/1975 | Franklin | 177/208 |
| 4,476,722 | 10/1984 | Bentkowski | 73/434 |
| 4,549,428 | 10/1985 | Murbach et al. | 73/32 R |

Primary Examiner—Stewart J. Levy
Assistant Examiner—John E. Chapman, Jr.
Attorney, Agent, or Firm—Kanz, Scherback & Timmons

[57] ABSTRACT

Disclosed is a method and apparatus for measuring the density of a liquid, such as a drilling mud, by continuously flowing a smaple of the liquid through a container having a fixed predetermined volume. The container is supported by at least one bed of pressurized fluid. The pressure of the fluid is varied in response to fluctuations in the weight of the liquid sample in the container. A pressure transmitter monitors the pressure level in the bed and produces a signal indicative of the density of the liquid sample.

21 Claims, 5 Drawing Figures

METHOD AND APPARATUS FOR MONITORING THE DENSITY OF A LIQUID

FIELD OF THE INVENTION

The present invention relates generally to methods and apparatus for monitoring the density of liquids, and more particularly, to methods and apparatus for monitoring the density of well drilling liquids.

BACKGROUND OF THE INVENTION

It is frequently useful to monitor the density of a liquid used in industrial processes. For instance, during drilling operations of a well bore, drilling mud is circulated through the drill pipe and the annulus of the well bore. The drilling mud serves several purposes in the drilling process, including lubrication and cooling of the drill bit and the removal of cuttings resulting from the penetration of the subsurface formations. Additionally, the weight of the drilling mud in the well bore exerts hydrostatic pressure on the subsurface formations that acts to contain the subsurface pressure encountered during drilling operations. These subsurface pressures may be extremely high, such as 8,000-10,000 psi, or the equivalent of two (2) pounds per square inch per foot of depth. If the hydrostatic pressure of the drilling mud at the depth at which the subsurface pressure is encountered is not equal to or greater than the subsurface pressure, the reservoir fluid will emerge from the subsurface formation and travel to the surface through the well bore. This is known as a blow out and creates extremely dangerous conditions as the pressurized formation fluid generally containing gas rapidly expands as it approaches the surface and atmospheric pressure. However, if the drilling mud hydrostatic pressure is too high, the subsurface formations may be fractured resulting in extensive loss of the relatively expensive drilling mud into the formations surrounding the well bore. Thus, the density of the drilling must must be monitored and adjusted if necessary, to maintain it within a desired range during drilling operations. Another constraint on the density of the drilling mud is that an increase in the density tends to reduce the penetration of the drill bit.

Drilling mud is a liquid composition, usually utilizing oil or water as a base to which various substances are added depending on the properties desired in the drilling operations, the subsurface and environmental conditions, as well as other factors as are known in the art. Typically, the additives include solid particulates or clays to promote the formation of a filter cake on the walls of the well bore and to assist in suspending the cuttings until the drilling mud containing the cuttings reaches the surface, and weighting material ssuch as barites, to control the density of the drilling mud. After circulation through the well bore, the drilling mud is filtered to remove the cuttings carried from the bottom of the well bore and then stored in a mud pit for subsequent use.

Under conventional drilling techniques, a small sample of the drilling mud is periodically obtained as it is deposited in the mud pit. The density of the sample is measured and a determination made whether or not to adjust the density of the drilling mud being used in the well bore. Existing apparatus used to measure the density of the drilling mud sample is called a mud balance and consists of a container having a known volume on one end and a scale and weight on the other end. The apparatus (i.e. mud container, scale and weight) is then placed on a knife edge fulcrum. The container is then filled to its capacity with the sample of interest. The weight is moved along the scale until balanced. Indicia on the scale at the location of the weight indicate the density of the mud sample. That is, the observed weight of the sample may be used to derive a measure of density by dividing the weight by the known volume of the container. The same scale can be calibrated in any set of units desired.

However, this and other conventional density monitoring procedures exhibit certain limitations. For instance, the monitoring of the drilling mud density is performed on an intermittent basis, and must be manually performed. This manual operation takes approximately 10-15 minutes. When conditions are encountered that cause rapid changes in the mud density, the density may drastically change in a matter of minutes or seconds. Frequently, it is not economical or practical to weigh samples of the drilling mud on an ongoing basis, since a skilled technician or engineer is required to perform the test. Less frequent samples introduce a time lag into the monitoring process that is undesirable. Further, manual weighing of a drilling mud sample on a mud balance is relatively inaccurate and requires visual interpretation, thereby introducing the possibility of human error. Finally, weighing of the drilling mud sample must be performed on site and cannot conveniently be conducted remotely. None of the existing methods or apparatus for monitoring drilling mud density adequatley solve the problems outlined above.

SUMMARY OF THE INVENTION

This invention provides a method and apparatus to measure the density of a liquid on a continuous basis, such as drilling mud returning from circulation in a well bore. The physical principal utilized is that a fore (F) is proportional to pressure (P) and area (A), where F equals the force in pounds and P equals pressure in PSI and A equals area in square inches. A continuous sample of the drilling mud is flowed through a container having a fixed predetermined volume. The container and the sample of the liquid is supported on at least one bed of pressurized fluid. The pressure of the fluid is varied by fluctuations in the weight of the container and liquid sample, so as to equalize the forces acting across the seal of the valve. A pressure transmitter is connected to the chamber and generates a continuous electrical signal indicative of the instantaneous pressure in the bed of pressurized fluid required to support the container and liquid sample. The electrical signal from the pressure transmitter is converted to a measure of the density of the drilling mud by electronically dividing it by a constant signal representative of the volume of the container cavity. Preferably, the valve is a spherical valve and acts to automatically maintain the container in an upright position, and is designed to have negligible pressure drop across the seal of the valve.

Therefore, it is a principal feature and advantage of this invention to provide an improved method and apparatus for continuously monitoring the density of a liquid.

It is another feature and advantage of this invention to provide an iproved method and apparatus for instantaneously and automatically monitoring the density of a liquid.

It is another feature and advantage of this invention to provide an improved method and apparatus for monitoring the density of a liquid in which the density of the liquid made way be remotely monitored.

BRIEF DESCRIPTION OF THE DRAWINGS

So that the manner in which the above recited features and advantages of the invention, as well as others which will become apparent to those skilled in the art, are obtained and can be understood in detail, a more particular description of the invention briefly summarized above may be had by reference to the embodiments thereof which are illustrated in the accompanying drawings, which drawings form a part of the specification and in which like numerals depict like parts in the several views. It is noted, however, that the appended drawings illustrate only a preferred embodiment of the invention and are therefore not to be considered limiting of its scope, for the invention may admit to other equally effective embodiments.

DETAILED DESCRIPTION OF THE INVENTION

Figure 1:
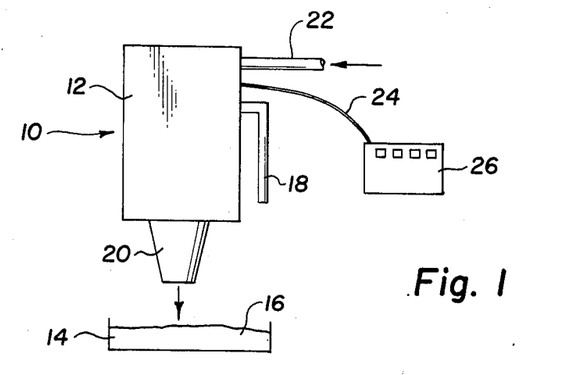
FIG. 1 is a schematic representation of a desnity measuring device according to this invention.

Referring now to FIG. 1, the reference numeral 10 generally indicates the apparatus of this invention, including generally rectangular housing or enclosure 12. The housing is positioned over mud pit 14 containing a quantity of drilling mud 16. Drilling mud intake pipe 18 is connected at one end (not shown) to the circulation system (not shwon) for the drilling mud and is adapted to continually convey to the housing a sample before the drilling mud is returned to the mud pit. Drilling mud outlet 20 extends downwardly from the bottom of the housing and is positioned to return the sample stream of drilling mud to the mud pit after exiting from the housing. Pressurized fluid conduit 22 is connected at one end (not shown) to a source of pressurized fluid (not shown). Although air may be utilized as the lfuid, any suitable fluid may be utilized within conduit 22 if desired. The other end of the fluid conduit extends into the interior of the housing, as will be explained hereinafter. Wire or cable 24 extends outwardly of the housing and is remotely connected to meter 26 for providing a display indicative of the density of the drilling mud sample.

Figure 2:
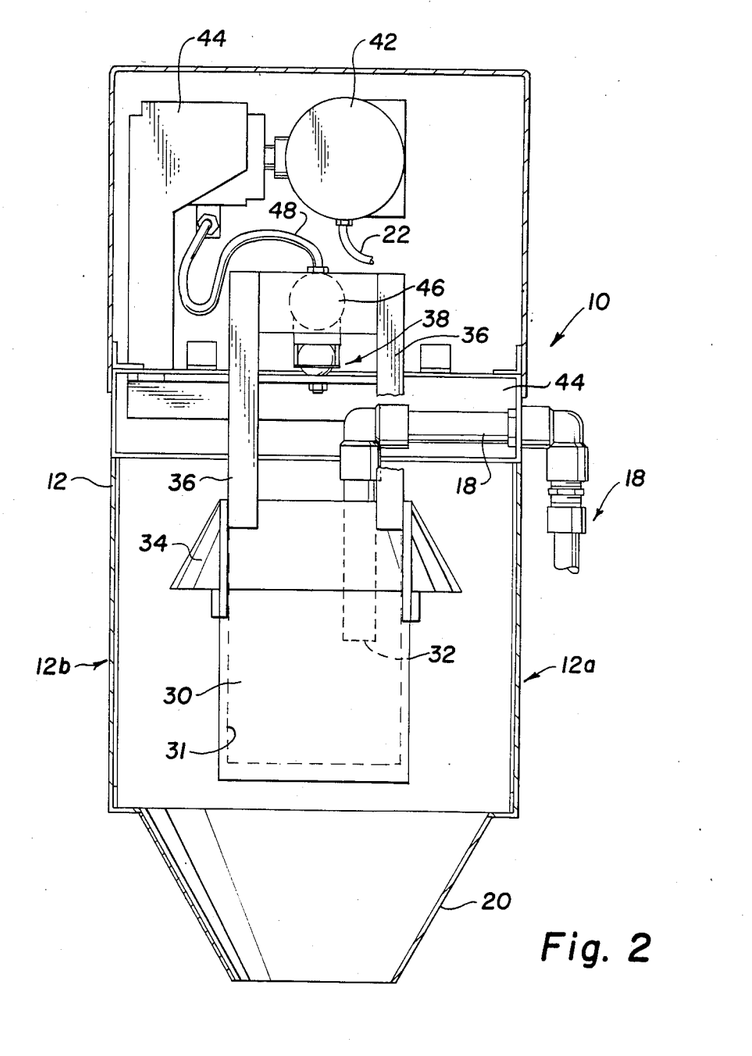
FIG. 2 is a front view, partially in cross section, of a density measuring device according to this invention.
Figure 3:
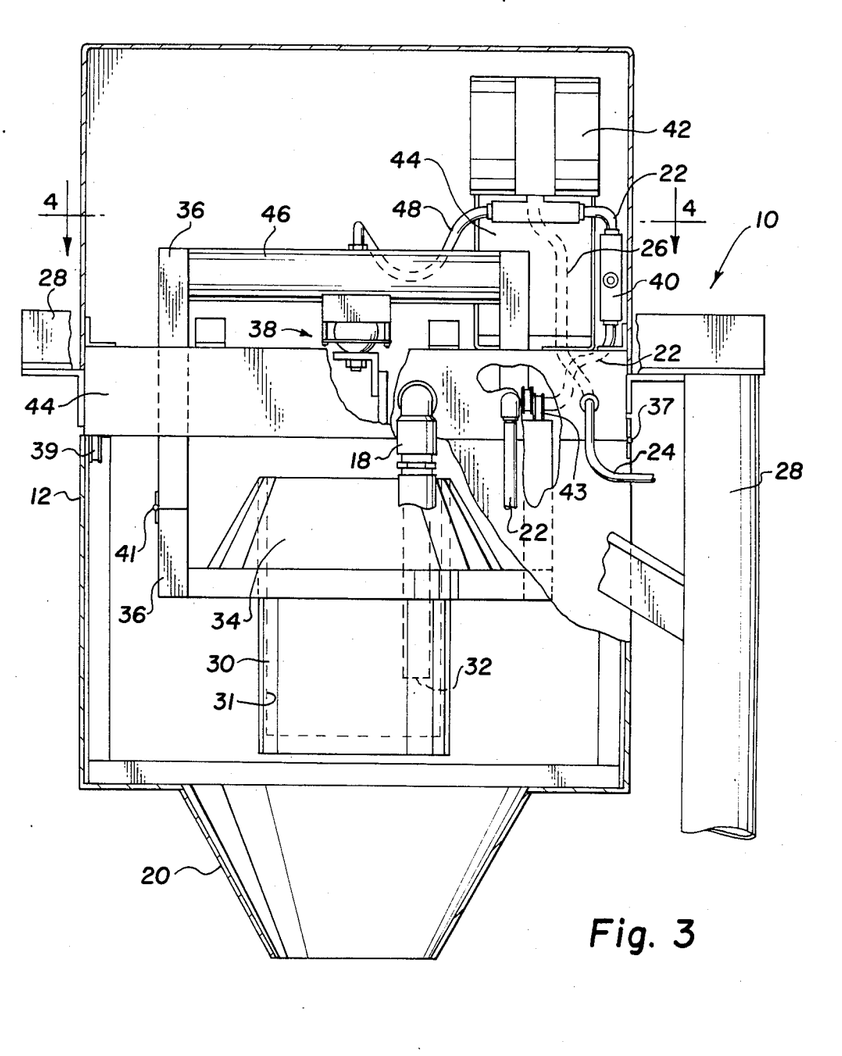
FIG. 3 is a side view, partially in cross section, of the density measuring device of FIG. 2.
Figure 4:
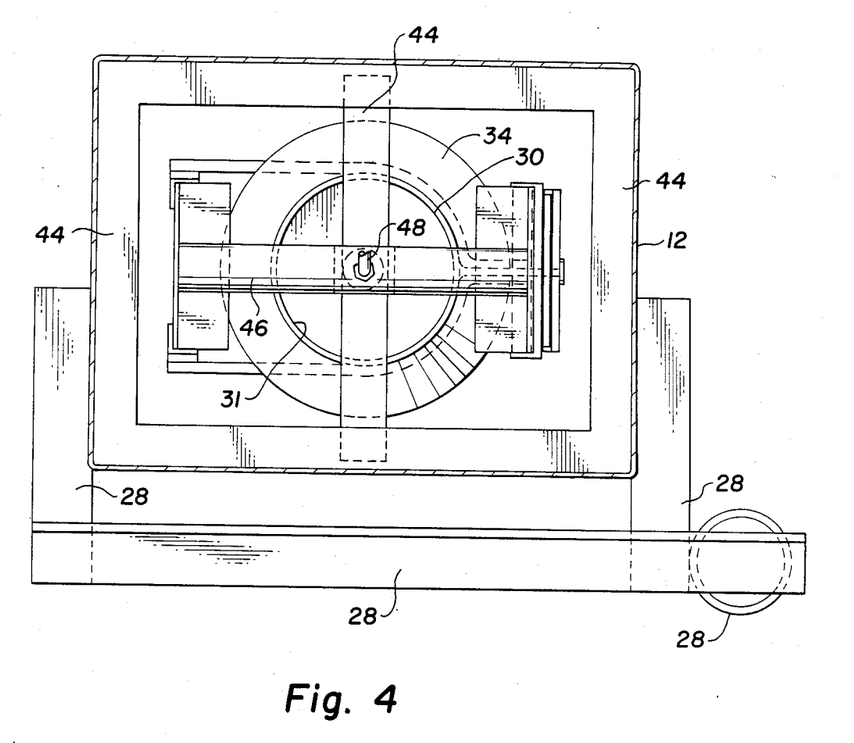
FIG. 4 is a cross sectional view along view 4—4 of the density measuring device of FIG. 3.

Turning now to FIGS. 2-4, the housing is shown in greater detail mounted on rigid external framework 28 (not a part of the apparatus) which consists of interconnected beams and trusses and is provided to support the housing over the mud pit (not shown). Housing 12 includes top, bottom, front and back walls and defines left and right sides, 12a and 12b, respectively, as seen in FIG. 2. Container 30 is provided within the housing to receive a continuous sample of the drilling mud. The container consists of a cylindrical body with an open upper end communicating with cavity 31 therewithin having a fixed and predetermined volume. Drilling mud is continuously introduced into the cavity of the container through drilling mud intake pipe 18, which does not contact container 30 at any place. Preferably, orifice 32 of the drilling mud intake pipe is located at a point below the upper rim of the container and the incoming drilling mud is pressurized sufficiently to maintain the entire volume of the cavity completely filled with the drilling mud at all times. If necessary, a pump (not shown) may be interposed into the drilling mud intake pipe upstream of the housing.

The drilling mud is most conveniently induced to overflow the upper end of the container and spill downwardly therefrom. Referring now again to FIG. 1, it will be seen that the drilling mud spilling from the container will fall through drilling mud outlet 20 and be returned to the mud pit on a continuous basis. As previously explained, drilling mud usually contains various additives. If the drilling mud is allowed to run down the sides of the container, these additives will have a tendency to be deposited on the container and to accumulate thereon, adding to the weight of the container and thereby introducing errors into the density measurement of the drilling mud. To prevent this accumulation, splash guard 34 is mounted on the upper rim of the container and flares outwardly and downwardly therefrom. The splash guard acts to direct the drilling mud spilling over from the container away therefrom and into the drilling mud outlet. The container and splash guard are mounted on support 36 which extends upwardly within the apparatus housing. The container support is connected to valve 38, as will be explained in greater detail hereinafter.

Even with the splash guard, it may be desirable to periodically clean or inspect the container or other portions of the apparatus. To accomplish this in the illustrated embodiment, the entire lower portion of the housing is constructed as a unitary structure hinged at 37 (shown in FIG. 3) along the back side thereof and secured by latch 39 on the front side, which may be magnetic latch. Further, support 36 includes a lower portion secured to the container and splash guard and hinged at 41 along its front side and secured by latch 43, which may be a magnetic latch. When cleaning or inspection of the container is desired, the lower portion of the housing is released and rotated in a counter clockwise direction (as seen in FIG. 3), exposing the container. The lower portion of the support is released and rotated in a clockwise direction, bringing the container outside of the housing and providing ready access. Reversal of the above procedure places the container in position to resume monitoring operations.

Pressurized fluid conduit 22 enters the housing through its back wall and extends to pressure regulator 40 mounted on the interior of the housing. The pressure regulator reduces the pressure of the fluid in the apparatus downstream of the pressure regulator to a level convenient for the purposes hereinafter described. Although not shown, the pressure regulator may include a pressure guage to aid in adjusting the output of the pressure regulator to desired levels. Conduit 22 extends from the outlet of the pressure regulator to pressure transmitter 42 mounted on internal framework 44 mounted on the housing. The pressure transmitter is sensitive to the pressure of the lfuid in the conduit downstream of the pressure regulator and generates a continuous electrical signal indicative of the pressure. The electrical signal from the pressure transmitter is conveyed externally of the housing by wire 24 to meter 26, where the calibrated pressure reading of the pressure transmitter is electronically converted to a signal, displayed by the meter, which is a measurement of the liquid density, as will be explained hereinafter. Pressure reservoir 46 is mounted on an upper portion of the container support over the valve. Conduit 48 extends from the pressure transmitter to the pressure reservoir to convey the pressurized fluid to the pressure reservoir.

Figure 5:
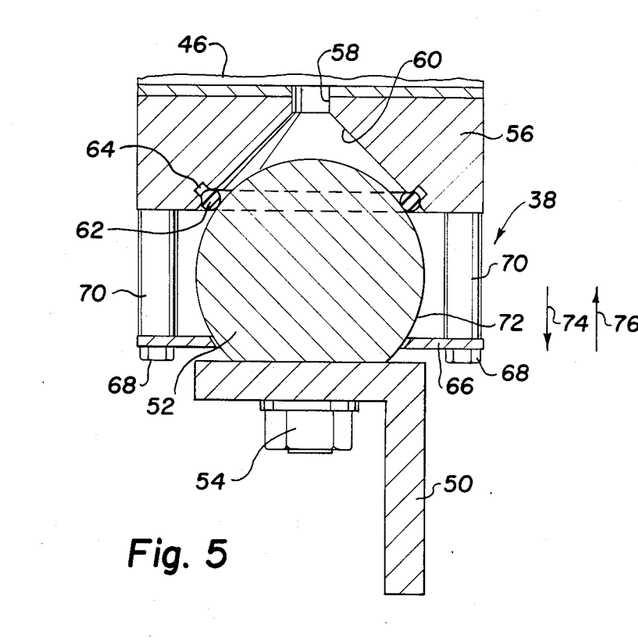
FIG. 5 is a magnified view of the ball valve of FIG. 3.

FIG. 5 shows in detail the construction of valve 38. Bracket 50 is mounted on internal framework 44 of the housing. Valve member 52 is mounted on the bracket, such as by bolt 54 or any other conventional means. In the preferred embodiment of the invention, the valve member is spherical, as shown in FIG. 5. Upper valve portion 56 is mounted on the under side of pressure reservoir 46. The upper valve portion includes conduit 58 communicating with the pressure reservoir and terminating in conical valve seat 60. The valve seat includes O-ring seal 62 mounte din annular groove 64 of the valve seat. The valve member is partially located within the valve seat adjacent the seal and is loosely restrained therewithin by retaining plate 66 mounted on the upper valve portion by bolts 68 and secured by spacers 70 carried about each of the bolts 68. The retaining plate includes concentric opening 72 of lesser diameter than the diameter of the valve member. The spacers 70 enable limited vertical movement of the upper valve portion, bolts, spacers, and retaining plate with respect to the valve member in directions 74 (downward) and 76 (upward). The upper valve portion is inherently urged downwardly in direction 74 into sealing engagement with the valve member by the combined weight of the container, container support, pressure reservoir, pressure transmitter, and the weight of the drilling mud sample carried by the container. It is one of the advantages of the spherical valve member that is inherently acts with the conical valve seat to center the support and the container and maintain the container in an upright and level position over the drilling mud outlet. The container is thus maintained in an upright and level position and the sample of drilling mud prevented from overflowing the container at a greater rate than the drilling mud is injected into the cavity.

In operation, a continuous stream of the drilling mud is injected into the cavity through the orifice of the drilling mud input pipe at a regulated flow rate, completely filling the cavity at all times. The contents of the container at any given time constitutes a representative and timely sample of the drilling mud emerging from the well bore. The rate of flow through the input pipe is adjusted, so that the pace of sampling may be any selected pace. For instance, should the chamber of the container have a capacity of 1 gallon and the desired pace of the sampling be one minute intervals, then the flow rate into the container would be adjusted to a rate to 1 gallon per minute. The drilling mud is injected within the cavity of the container at sufficient pressure so that the sample stream continuously flows upward through the cavity and overflows the container onto the splash guard, through the drilling mud outlet and into the mud pit. At the same time, pressurized fluid is introduced into pressure reservoir 46 through conduits 22 and 48, pressure regulator 40 and presure transmitter 42. The pressurized fluid is introduced into the upper valve portion of the spherical valve through conduit 58 and acts against the surface of the valve member above the O-ring seal to lift the container and the container support upwards in direction 76, limited by contact between the lower part of the valve member and the retaining plate. If the combined weight of the container, support, and the sample of drilling mud contained in the cavity is less than or equal to the force of the pressurized fluid acting on the valve, then the valve will remain closed. However, if the force of the pressurized fluid on the valve member exceeds the weight of the container, support, and the sample of drilling mud contained in the cavity, then the valve will be opened and the fluid will be vented from the reservoir through the valve. This venting will continue until the pressure in the pressure reservoir is reduced to a point that the force exerted on the valve is sufficient to maintain the valve slightly open with a relatively small constant rate of fluid being vented, thereby creating a stable pressure in the pressure reservoir. Thus, the pressure of the fluid in the pressure reservoir will rapidly assume the equilibrium level determined by the combined weight of the container, support, and the sample of drilling mud contained int he cavity. Of course, the pressurized fluid as controlled by the pressure regulator, must be supplied to the pressure reservoir at a level high enough to open the valve for all anticipated drilling mud densities.

Since the weight of the container, pressure reservoir, pressure transmitter and the support is fixed and predetermined, any fluctuation in the force urging the valve towards a closed position, as measured by the instantaneous equilibrium pressure within the pressure reservoir, must be due to changes in the weight of the drilling mud sample in the cavity of the container. Because the volume of the cavity is also fixed and predetermined, the weight of the sample varies as the density of the drilling mud varies. The electrical signal of the pressure transmitter is indicative of the weight of the drilling mud sample. Since the volume of the cavity is known, the signal from the pressure transmitter may be electronically divided by a fixed electrical signal representative of the cavity volume, in a manner known in the art, to achieve a measurement of the drilling mud density, which is displayed on the meter, which may be remotely located with respect to the remainder of the apparatus. Alternatively, the density measurement may be recorded for future use, in lieu of or in addition to display on the meter.

Thus, the apparatus and method of the present invention enables the density of the drilling mud returning from the well bore to be monitored on a continuous basis and is instantly responsive to fluctuations in that density, indicative of downhole conditions. Further, monitoring operations may be conducted automatically and controlled remotely, and provides a more accurate and consistent measurement than conventional systems.

Although the invention has been disclosed above, with regard to particular and preferred embodiments, these are advanced for illustrative purposes only, and are not intended to limit the scope of this invention. For instance, although the invention has been described as having a single bed of pressurized fluid above the container and from which the container is suspended, the invention may employ more than one bed of pressurized fluid or the bed or beds may be located below or to the side of the container. Further, although the spherical valve is utilized as having self centering features in order to maintain the container in an upright and level position, other types of valves may be used and separate means employed to maintain the container in an upright and level position. Finally, the invention is not limited to monitoring of drilling mud density, but may be applied to various other liquids. These variations remain within the invention as claimed below.

What is claimed is:

1. A method of continually monitoring the density of a liquid, comprising the steps of:
   (a) continually obtaining samples of the liquid;
   (b) flowing the samples into a container having a closed bottom and sides;
   (c) overflowing the container so as to maintain a fixed predetermined volume of the liquid samples within the container;
   (d) supporting the container and liquid samples on at least one bed of pressurized lfuid; and
   (e) varying the pressure of the fluid as a function of the weight of the container and liquid to produce a signal representative of the density of the liquid.

2. The method of claim 1 further comprising the step of deflecting the overflowing liquid samples from the container so as to prevent the accumulation of teh liquid on the sides of the container.

3. The method of claim 1, in which the liquid samples are flowed into the container at a point below an upper end of the container, thereby causing a continuous change in the contents of the container.

4. The method of claim 1, in which the liquid is a drilling mud which has been returned from the well bore to a mud pit at the surface and in which the drilling mud is sampled prior to its return to the mud pit and further in which the overflow from the container is returned to the mud pit.

5. The method of claim 1, in which the bed of pressurized fluid is established above the container.

6. Apparatus for continuously monitoring the density of a liquid, comprising:
   (a) a container having a closed bottom and sides;
   (b) means for continuously obtaining samples of the liquid;
   (c) means for flowing the samples of the liquid into said container;
   (d) means for maintaining a fixed predetermined volume of the liquid samples in said container by overflowing the container;
   (e) means for providing at least one bed of pressurized fluid;
   (f) means for supporting said container and the liquid samples on said bed of pressurized fluid and means for varying the pressure of the lfuid as a function of the weight of the container and the liquid to produce a signal representative of the density of the liquid.

7. The apparatus of claim 6, in which said means for supporting said container on said bed of pressurized fluid includes:
   (a) a housing;
   (b) a structure having a spherical outer surface mounted in fixed relation to said housing; and
   (c) a support having an upper portion supported solely on said spherical structure and a lower portion for receiving said container, whereby said support may move about said spherical structure to amintain said container in a horizontal position relative to the earth's surface.

8. The apparatus of claim 6, further including means formed at the top of said container for directing overflow of liquid from said container away from outer sides of the container to avoid buildup of any sediments in the liquid on the outer sides of said container.

9. The apparatus of claim 8, wherein said means for directing the overflow of the liquid from said container is an annular lip depending outwardly and downwardly from said container.

10. Apparatus for continuously monitoring the density of a liquid, comprising:
    (a) a housing including a source of pressurized fluid;
    (b) a container having a closed bottom and sides and defining a fixed predetermined volume for receipt of the liquid;
    (c) means for continuously flowing a sample of the liquid into said container, said continuous sample filling said volume within container and continuously overflowing said container;
    (d) at least one bed of pressurized fluid mounted on said housing and ocnnected to said source of pressurized fluid, said container being solely supported by said bed by varying the pressure level of said fluid responsive to the weight of said container and said sample of the liquid; and
    (e) means for continuously measuring the value of fluid pressure in said bed necessary to support said container and liquid sample and generating a signal indicative of the density of the liquid.

11. The apparatus of claim 10, wherein said bed of pressurized fluid includes a valve mounted on said housing urged to a closed position by the weight of said container and said sample of the liquid, said valve being connected to said source of pressurized fluid and urged to an open position by said pressurized fluid, so ast o continuously vary the value of pressure of said fluid responsive to fluctuations in the weight of said container and said smaple of liquid thereby equalizing the forces acting on said valve.

12. The apparatus of claim 11, wherein said valve is automatically self centering.

13. The apparatus of claim 11, wherein said valve is a spherical valve.

14. The apparatus of claim 11, wherein said container is suspended from said valve and including means for automatically and continuously maintaining said container in an upright and level position.

15. The apparatus of claim 10, wherein said measuring means comprises a pressure transmitter connected to said source of pressurized fluid and adapted to generate an electrical signal indicative of the density of the liquid.

16. The apparatus of claim 10, wherein said source of pressurized fluid is a pressure reservoir mounted on said housing.

17. The apparatus of claim 10, further comprising means formed at the top of said container for directing overflow of liquid from said container away from its outer sides to avoid build-up of any sediment in the liquid on the outer side of said container.

18. The apparatus of claim 17 wherein said means for directing the overflow of liquid from said container is an annular lip extending downwardly and outwardly from said container.

19. Apparatus for continuously measuring the density of a drilling mud being returned to a mud pit after circulation through a well bore, comprising:
    (a) a housing;
    (b) a container having a closed bottom and sides and defining a fixed predetermined volume;
    (c) means for continuously filling said container with a sample of the circulated drilling mud prior to its return to the mud pit and further in which the overflow from the container is returned to the mud pit, said means injecting said sample into said container at a point below an upper end of the container and in which a predetermined volume of the drilling mud is maintained in said container by overflowing the sides of the container;

(d) means formed at the top of said container for directing overflow of drilling mud away from the sides of the container to avoid buildup of sedimetns in the drilling mud on the sides of said container;

(e) means for establishing a bed of pressurized fluid, said means being mounted on said housing above said container and adapted for connection to a source of pressurized fluid, said container being supported from said means by varying the pressure of said fluid responsive to the weight of said container and said sample of the liquid; and (f) a pressure establishing a bed to said means for establishing a bed of pressurized fluid for generating an electrical signal responsive to the pressure of the fluid in the bed indicative of the density of the liquid.

20. The apparatus of claim 19, wherein said bed includes a valve mounted on said housing urged to a closed position by the weight of said container and said sample of the liquid, said valve being connected to the source of pressurized fluid and urged to an open position by said pressurized fluid in said bed of pressurized fluid, so as to continuously vary the pressure of said fluid responsive to fluctuations in the weight of said container and said sample of liquid, thereby equalizing the forces acting on said valve.

21. The apparatus of claim 19, in which said means formed at the top of said container for directing overflow of liquid from said container away from its outer sides to avoid buildup of any sediments in the liquid on the outer sides of said container comprises an annular lip extending downwardly and outwardly from said container.

* * * * *

UNITED STATES PATENT AND TRADEMARK OFFICE
CERTIFICATE OF CORRECTION

PATENT NO. : 4,677,851  Page 1 of 2

DATED : July 7, 1987

INVENTOR(S) : James A. McAuley

It is certified that error appears in the above-identified patent and that said Letters Patent is hereby corrected as shown below:

In the Abstract, line 3, change "smaple" to -- sample --.
In column 1, line 39, change "must" to -- mud --.
In column 1, line 53, change "material ssuch" to -- materials such --.
In column 2, line 37, change "fore" to -- force --.
In column 2, line 64, change "iproved" to -- improved --.
In column 3, line 19, change "desnity" to -- density --.
In column 3, line 38, change "shwon" to -- shown --.
In column 3, line 46, change "lfuid" to -- fluid --.
In column 4, line 36, after "be", insert -- a --.
In column 4, line 61, change "lfuid" to -- fluid --.
In column 5, line 17, change "mounte din" to -- mounted in --.
In column 5, line 34, change "is" to -- it --.
In column 5, line 54, change "to" to -- of --.
In column 6, line 18, change "int he" to -- in the --.
In column 7, line 11, change "lfuid" to -- fluid --.
In column 7, line 17, change "teh" to -- the --.
In column 7, line 46, change "lfuid" to -- fluid --.
In column 7, line 60, change "amintain" to -- maintain --.
In column 8, line 14, change "ocnnected" to -- connected --.
In column 8, line 28, change "ast o" to -- as to --.
In column 8, line 31, change "smaple" to -- sample --.
In column 9, line 7, change "sedimetns" to -- sediments --.

UNITED STATES PATENT AND TRADEMARK OFFICE
CERTIFICATE OF CORRECTION

PATENT NO. : 4,677,851           Page 2 of 2

DATED     : July 7, 1987

INVENTOR(S) : James A. McAuley

It is certified that error appears in the above-identified patent and that said Letters Patent is hereby corrected as shown below:

In column 9, line 18, change "establishing a bed" to

-- transmitter connected --.

Signed and Sealed this

Seventeenth Day of November, 1987

*Attest:*

DONALD J. QUIGG

*Attesting Officer*     *Commissioner of Patents and Trademarks*